United States Patent
Chen et al.

(10) Patent No.: US 6,569,695 B1
(45) Date of Patent: May 27, 2003

(54) METHOD FOR MONITORING PARTICLES AND DEFECTS ON WAFER SURFACE AND IN PROCESS

(75) Inventors: Shih-Yen Chen, Hsinchu (TW); Chao-Chuan Tseng, Hsin Chu (TW)

(73) Assignee: Macronix International Co., Ltd., Hsinchu (TW)

( * ) Notice: Subject to any disclaimer, the term of this patent is extended or adjusted under 35 U.S.C. 154(b) by 0 days.

(21) Appl. No.: 10/104,329

(22) Filed: Mar. 22, 2002

(30) Foreign Application Priority Data

Feb. 25, 2002  (TW) ........................... 91103245 A

(51) Int. Cl.⁷ .......................... H01L 31/26; H01L 21/66
(52) U.S. Cl. ........................................ 438/14; 438/36
(58) Field of Search .................... 438/14, 199, 230, 438/231, 232, 305, 306

(56) References Cited

U.S. PATENT DOCUMENTS 5,936,726 A * 8/1999 Takeda et al.
6,103,563 A * 8/2000 Lukanc et al.

* cited by examiner

Primary Examiner—David Nelms
Assistant Examiner—Phuc T. Dang
(74) Attorney, Agent, or Firm—J. C. Patents

(57) ABSTRACT

A method for monitoring particles and defects on a wafer surface and in a process is described, which uses a monitoring instrument to detect particles and defects possibly present on a substantially effective surface of a wafer. Before the monitoring step, a substantially uniform conformal layer is formed on the substantially effective surface of the wafer, wherein the thickness of the conformal layer is controlled so that the apparent sizes of the particles and the defects possibly present on the wafer surface can be increased moderately.

14 Claims, 1 Drawing Sheet

METHOD FOR MONITORING PARTICLES AND DEFECTS ON WAFER SURFACE AND IN PROCESS

CROSS-REFERENCE TO RELATED APPLICATION

This application claims the priority benefit of Taiwan application serial no. 91103245, filed Feb. 25, 2002.

BACKGROUND OF THE INVENTION

1. Field of Invention

The present invention relates to a method for monitoring a semiconductor process. More particularly, the present invention relates to a method for monitoring particles and defects on a wafer surface and in a process.

2. Description of Related Art

In a semiconductor process, monitoring steps are usually conducted to monitor particles and defects on a wafer after some critical fabricating steps. Since the particles and the defects generated in the critical fabricating steps will significantly deteriorate the quality of the device, the monitoring steps are quite important for a semiconductor process.

In the prior art, a monitoring step is conducted directly after a critical fabricating step, wherein the particles and the defects on a wafer are detected with a monitoring instrument.

However, when the size of a particle or a defect on a wafer surface is smaller than the detecting limit (~0.1 μm) of current monitoring instruments, the particle or the defect cannot be detected. This problem is troublesome especially for the fabrication of smaller devices in a highly integrated product since tiny defects or particles will deteriorate the quality of the device significantly.

SUMMARY OF THE INVENTION

In view of the above-mentioned problem, this invention provides a method for monitoring particles and defects on a wafer surface and in a process to improve the detecting sensitivity of defects or particles.

In the method for monitoring particles and defects on a wafer surface of this invention, a monitoring instrument is used to monitor the particles/defects possibly present on a substantially effective surface of the wafer, wherein the particles/defects include those with sizes smaller than 0.1 μm. Before the monitoring step, a substantially uniform conformal layer is formed on the wafer, wherein the thickness of the conformal layer is controlled so that the apparent sizes of the particles/defects possibly present on the surface can be increased moderately. The conformal layer may comprise silicon nitride, polysilicon or silicon oxide, and may be formed in a thermal process common centura using rapid thermal process (RTP) deposition for only 6~10 minutes to have a thickness from 1000 Å to 2000 Å, for example.

This invention further provides a method for monitoring particles and defects possibly generated in a process to estimate the amount of the particles/defects possibly generated in a fabricating machine during a real production. In this method, a dummy wafer is placed into the fabricating machine to be processed under the same conditions as in the real production. A substantially uniform conformal layer is formed on the dummy wafer, wherein the thickness of the conformal layer is controlled so that the apparent sizes of the particles/defects possibly present on the surface can be increased moderately. The conformal layer may comprise silicon nitride, polysilicon or silicon oxide, and may be formed in a thermal process common centura using rapid thermal process (RTP) deposition for only 6~10 minutes to have a thickness from 1000 Å to 2000 Å, for example. Subsequently, a monitoring instrument is used to detect the surface of the conformal layer to monitor the particles/defects possibly present on the surface.

Since the apparent sizes of the particles or the defects on a (dummy) wafer surface are increased with the conformal layer formed thereon, a particle or a defect having originally a size smaller than the detecting limit of the monitoring instrument can be detected. Therefore, by using the method of this invention, the detecting sensitivity problem encountered in the prior art can be solved.

Moreover, since the conformal layer is formed on the (dummy) wafer surface in a thermal process common centura using rapid thermal process (RTP) deposition in this invention, it takes only 6~10 minutes to form a thickness from 1000 Å to 2000 Å. Therefore, the method of this invention just takes a little more time than before.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings, FIGS. 1A~1B schematically illustrate a method for monitoring particles and defects on a wafer or in a process according to a preferred embodiment of this invention in a cross-sectional view.

DESCRIPTION OF THE PREFERRED EMBODIMENTS

Figure 1A:
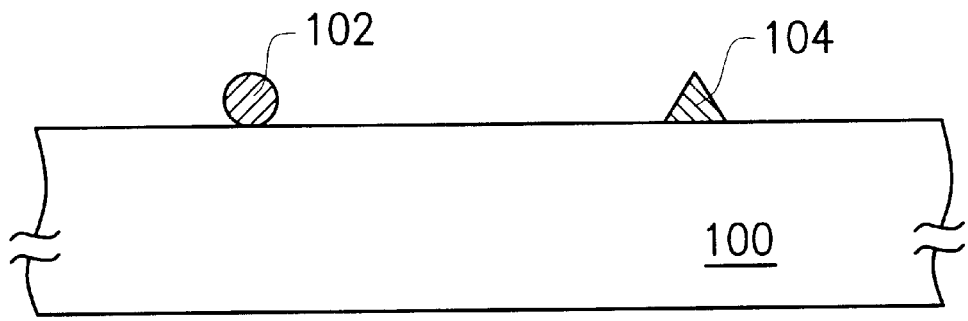

Refer to FIG. 1A, a wafer 100 is provided, which is a wafer during processing or a dummy wafer for testing. When the wafer 100 is during processing, the method of this invention can be used to monitor the formation of particles and defects on a substantially effective surface of the wafer. When the wafer is a dummy wafer, it can be placed into a fabricating machine to be processed under the same conditions as those in a real production, so as to estimate the amount of the particles/defects possibly generated in the fabricating machine during the production. The particle 102 or the defect 104 may have a size smaller than 0.1 μm.

Figure 1B:
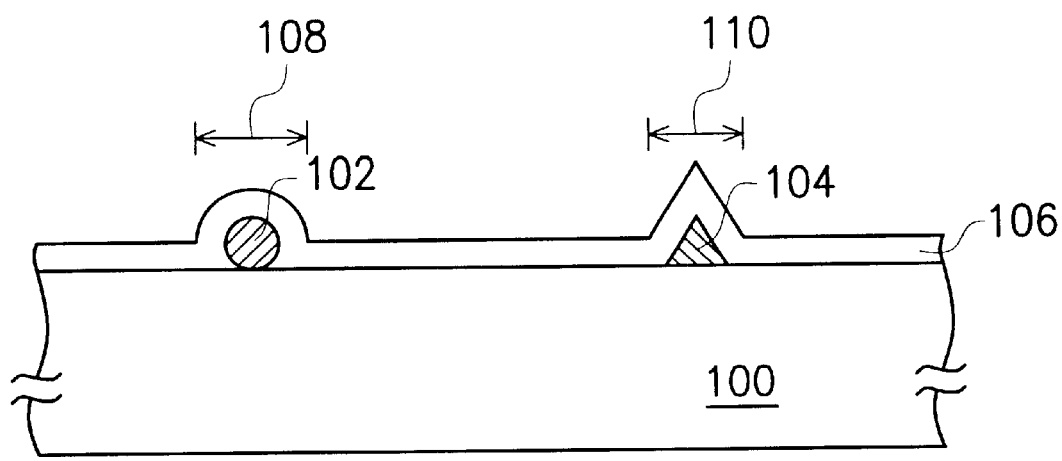

Refer to FIG. 1B, a substantially uniform conformal layer 106 is formed over the wafer 100 covering the particle 102 and the defect 104.

The conformal layer 106 may comprise a material such as silicon nitride, polysilicon or silicon oxide, and is formed in a thermal process common centura using rapid thermal process (RTP) deposition under a temperature from about 700° C. to about 800° C. and a pressure from about 250 Torr to about 300 Torr, for example. The thickness of the conformal layer 106 is, for example, about 1000 Å~2000 Å and the deposition time is only about 6~10 minutes in the case.

When the conformal layer 106 comprises silicon nitride, the reaction gases used in the rapid thermal process (RTP)

deposition are, for example, silane (SiH$_4$) and ammonia (NH$_3$), the pressure is about 275 Torr, and the deposition rate is about 33.33 Å/s, for example.

When the conformal layer 106 comprises silicon oxide, the reaction gases used in the rapid thermal process (RTP) deposition are, for example, silane (SiH$_4$) and dinitrogen oxide (N$_2$O), the pressure is about 275 Torr, and the deposition rate is about 1.16 Å/s, for example.

When the conformal layer 106 comprises polysilicon, the reaction gas used in the rapid thermal process (RTP) deposition is, for example, SiH$_4$, the pressure is about 275 Torr, and the deposition rate is about 30 Å/s, for example.

Refer to FIG. 1B again, due to the existence of the conformal layer 106 having a certain thickness, the apparent sizes of the particle 102 and the defect 104 are increased to be larger dimensions 108 and 110, respectively. This is useful especially for the particle 102 or the defect 104 having originally a size smaller than the detecting limit (0.1 $\mu$m) of current monitoring instruments because the apparent size of the particle 102 or the defect 104 can be increased to be larger than 0.1 $\mu$m. Therefore, a current monitoring instrument with a detecting limit of about 0.1 $\mu$m can be used to detect the particle 102 or the defect 104 having originally a size smaller than 0.1 $\mu$m.

Since the apparent sizes of the particles or the defects are increased with the conformal layer formed thereon, a particle or a defect having originally a size smaller than the detecting limit of the monitoring instrument can be detected.

Moreover, since the conformal layer can be formed in a thermal process common centura using rapid thermal process (RTP) deposition in this invention, it takes only 6~10 minutes to form a thickness from 1000 Å to 2000 Å. Therefore, the wafer monitoring method of this invention just takes a little more time than before.

It will be apparent to those skilled in the art that various modifications and variations can be made to the structure of the present invention without departing from the scope or spirit of the invention. In view of the foregoing, it is intended that the present invention covers modifications and variations of this invention provided they fall within the scope of the following claims and their equivalents.

What is claimed is:

1. A method for monitoring particles and defects on a wafer surface, the method using a monitoring instrument to monitor particles and defects possibly present on a substantially effective surface of a wafer and is characterized by the step of:

forming a substantially uniform conformal layer on the substantially effective surface of the wafer before the monitoring step, wherein a thickness of the conformal layer is controlled so that apparent sizes of the particles and the defects possibly present on the surface can be increased.

2. The method of claim 1, wherein the conformal layer is formed in a machine including a thermal process common centura used for rapid thermal process (RTP) deposition.

3. The method of claim 2, wherein the conformal layer is formed under a pressure from about 250 Torr to about 300 Torr.

4. The method of claim 2, wherein forming the conformal layer requires a period of time from about 6 minutes to about 10 minutes.

5. The method of claim 2, wherein a temperature for forming the conformal layer ranges from about 700° C. to about 800° C.

6. The method of claim 1, wherein a thickness of the conformal layer ranges from about 1000 Å to about 2000 Å.

7. The method of claim 1, wherein the conformal layer comprises a material selected from the group consisting of silicon nitride, polysilicon and silicon oxide.

8. A method for monitoring particles and defects in a process, the method being used to estimate an amount of particles and defects possibly generated in a fabricating machine during a real production and comprising the steps of:

placing a dummy wafer into the fabricating machine to be processed under the same conditions as in the real production;

forming a substantially uniform conformal layer on the dummy wafer, wherein a thickness of the conformal layer is controlled so that apparent sizes of the particles and the defects possibly present on the dummy wafer can be increased moderately; and using a monitoring instrument to detect the surface of the conformal layer to monitor the particles and the defects possibly present on the dummy wafer.

9. The method of claim 8, wherein the conformal layer is formed in a machine including a thermal process common centura used for rapid thermal process (RTP) deposition.

10. The method of claim 9, wherein the conformal layer is formed under a pressure from about 250 Torr to about 300 Torr.

11. The method of claim 9, wherein forming the conformal layer requires a period of time from about 6 minutes to about 10 minutes.

12. The method of claim 9, wherein a temperature for forming the conformal layer ranges from about 700° C. to about 800° C.

13. The method of claim 8, wherein a thickness of the conformal layer ranges from about 1000 Å to about 2000 Å.

14. The method of claim 8, wherein the conformal layer comprises a material selected from the group consisting of silicon nitride, polysilicon and silicon oxide.

* * * * *